(12) United States Patent
Vega et al.

(10) Patent No.: US 10,182,771 B2
(45) Date of Patent: Jan. 22, 2019

(54) METHOD AND SYSTEM FOR DOSE-OPTIMIZED COMPUTED TOMOGRAPHY SCANNING OF A TARGET ORGAN

(71) Applicant: Siemens Healthcare GmbH, Erlangen (DE)

(72) Inventors: Fernando Vega, Erlangen (DE); Frank Sauer, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 232 days.

(21) Appl. No.: 15/429,459

(22) Filed: Feb. 10, 2017

(65) Prior Publication Data
US 2018/0228450 A1  Aug. 16, 2018

(51) Int. Cl.
| A61B 6/03 | (2006.01) |
| A61B 6/04 | (2006.01) |
| A61B 6/00 | (2006.01) |
| A61B 6/02 | (2006.01) |

(52) U.S. Cl.
CPC .............. *A61B 6/032* (2013.01); *A61B 6/027* (2013.01); *A61B 6/0457* (2013.01); *A61B 6/488* (2013.01); *A61B 6/50* (2013.01); *A61B 6/5205* (2013.01); *A61B 6/5217* (2013.01); *A61B 6/545* (2013.01); *A61B 6/542* (2013.01)

(58) Field of Classification Search
None
See application file for complete search history.

(56) References Cited

U.S. PATENT DOCUMENTS

| 6,778,628 | B2 | 8/2004 | Yamazaki et al. |
| 7,602,880 | B2 | 10/2009 | Hirokawa et al. |
| 8,744,039 | B2 | 6/2014 | Hirokawa et al. |
| 9,524,582 | B2 | 12/2016 | Ma et al. |
| 2005/0041772 | A1* | 2/2005 | Nishide .................. A61B 6/032 378/19 |
| 2006/0036150 | A1 | 2/2006 | Lutz et al. |

(Continued)

FOREIGN PATENT DOCUMENTS

| JP | 2009039330 A | 2/2009 |
| WO | 2016073841 A1 | 5/2016 |

OTHER PUBLICATIONS

European Extension Search Report (EESR) dated Jul. 5, 2018 in corresponding European Patent Application No. 18155025.2.

*Primary Examiner* — Hoon K Song (57) ABSTRACT

A method and system for dose-optimized acquisition of a computed tomography (CT) scan of a target organ is disclosed. A localizer spiral CT scan is started at a beginning of a confidence range before a target organ. Real-time localizer scan images are automatically analyzed to predict a beginning location of the target organ based on the real-time localizer scan images. A diagnostic spiral CT scan is automatically started at the predicted beginning location of the target organ. Real-time diagnostic scan images are automatically analyzed to predict an end location of the target organ where full coverage of the target organ will be reached. The diagnostic spiral CT scan is automatically stopped in response to reaching the predicted end location of the target organ. A 3D profile can be acquired using a 3D camera and used to determine the confidence range before the target organ.

30 Claims, 3 Drawing Sheets

(56) References Cited

U.S. PATENT DOCUMENTS

| | | |
|---|---|---|
| 2007/0217567 A1 | 9/2007 | Noshi et al. |
| 2009/0141854 A1 | 6/2009 | Hirokawa et al. |
| 2010/0080434 A1 | 4/2010 | Seifert et al. |
| 2011/0091008 A1* | 4/2011 | Hirokawa .............. A61B 6/032 378/4 |
| 2015/0297157 A1 | 10/2015 | Mukumoto |
| 2018/0000439 A1* | 1/2018 | Kawanabe ........... A61B 6/5205 |
| 2018/0140270 A1* | 5/2018 | Profio .................... A61B 6/545 |

* cited by examiner

METHOD AND SYSTEM FOR DOSE-OPTIMIZED COMPUTED TOMOGRAPHY SCANNING OF A TARGET ORGAN

BACKGROUND OF THE INVENTION

The present invention relates to planning and acquisition of computed tomography (CT) scans of a target organ, and more particularly, to planning and acquisition of dose-optimized CT lung scans.

Computed tomography (CT) is a medical imaging technique that makes use of computer-processed combinations of many X-ray projection images taken from different angles to produce cross-sectional images of specific areas of a scanned object. CT can be used to generate a three-dimensional (3D) image of the inside of the scanned object from a series of two-dimensional projection images taken around a single axis of rotation. CT chest or lung scans can be used for detecting both acute and chronic changes in the lung parenchyma. For example, because CT is able to detect very small nodules in the lung, CT lung scans are often used for diagnosing lung cancer at its earliest, most curable stage.

CT scans expose patients to radiation, which can be harmful. Lung scans currently require topographic scans of the patient previous to the actual acquisition of the diagnostic CT lung scan. Such a topographic scan is used to obtain a topogram, which is a scout image obtained with a low dose of radiation at a low resolution that is used for planning the high-dose diagnostic scan. The topogram is typically a whole body flat sagittal section, obtained with the CT gantry stopped and the X-ray tube fixed at the upper position. Using the topogram, a series of manual steps is used to plan the scan range of the diagnostic CT lung scan to attempt to limit the exposure of the tissue beyond the lung to as little x-ray radiation dose as possible in the subsequent diagnostic CT scan. However, techniques to further limit the radiation dose that patients are exposed to during CT lung scans are desirable.

BRIEF SUMMARY OF THE INVENTION

The present invention provides a method and system for dose-optimized CT lung scan acquisition. Embodiments of the present invention provide a fully automated dose-optimized CT lung scan acquisition without the need for a tomogram acquisition and without incurring delays related to slow down and acceleration of the gantry rotation. Embodiments of the present invention utilize a 3D image obtained from a 3D camera, as well as real-time spiral scan data landmark detection to determine the scan range for CT lung acquisition.

In an embodiment of the present invention, a localizer spiral CT scan is started at a beginning of a confidence range before a target organ of a patient. Real-time localizer scan images are received from the localizer spiral CT scan as a patient is moved relative to a gantry of a CT scanning device. The real-time localizer scan images are automatically analyzed to predict a beginning location of the target organ based on the real-time localizer scan images. A diagnostic spiral CT scan is automatically started at the predicted beginning location of the target organ. Real-time diagnostic scan images are received from the diagnostic spiral CT scan as the patient is moved relative to the gantry of the CT scanning device. The real-time diagnostic scan images are automatically analyzed to predict an end location of the target organ where full coverage of the target organ will be reached based on the real-time diagnostic scan images. The diagnostic spiral CT scan is automatically stopped in response to reaching the predicted end location of the target organ.

In an embodiment of the present invention, a 3D profile of the patient on a table of the CT scanning device is acquired using a 3D camera, a patient model is fit to the 3D profile of the patient, and the beginning of the confidence range before the target organ of the patient is automatically determined based on the patient model.

These and other advantages of the invention will be apparent to those of ordinary skill in the art by reference to the following detailed description and the accompanying drawings.

DETAILED DESCRIPTION

The present invention relates to a method and system for dose-optimized acquisition of a CT scan of a target organ. Embodiments of the present invention are described herein to give a visual understanding of the methods for scan range determination and CT lung scan acquisition. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Lung scans currently require topographic scans of the patient previous to the actual acquisition of the diagnostic CT lung scan. Such a topographic scan is used to obtain a topogram, which is a scout projection image obtained with a low dose of radiation at a low resolution that is used for planning the high-dose diagnostic scan. In order to perform an ordinary lung scan, the patient typically lies on the table of the CT scanning device and the table is positioned to align the start position of the topogram scan at shoulder level of the patient. The gantry rotation must be slowed down and stopped, which may take 2 minutes. Once the gantry rotation has been stopped, the topogram image is then acquired. The topogram image is typically a projection section, obtained with the CT gantry stopped and the X-ray tube fixed at the upper position. The topogram acquisition is manually stopped after a radiologist determines that the lungs are completely covered by the topogram scan. Scan range planning is then manually performed on the topogram image to set the scan range for the diagnostic CT lung scan. The scan mode is then loaded and the gantry rotation is started, and the diagnostic CT lung scan is performed. The diagnostic CT acquisition is manually stopped after the radiologist determines that both lungs are completely acquired.

Embodiments of the present invention provide a fully automated dose-optimized CT lung scan acquisition without the need for a tomogram acquisition and without incurring delays related to slow down and acceleration of the gantry rotation. Embodiments of the present invention utilize a 3D image obtained from a 3D camera, as well as real-time spiral scan data landmark detection to determine the scan range for CT lung acquisition. Embodiments of the present invention allow a scanner to perform a lung examination from patient positioning to image reconstruction without manual intervention and without time penalties due to acceleration and/or stopping times for the gantry. Additionally, embodiments of the present invention reduce the total radiation dose as compared with the convention method of CT lung acquisition.

Figure 1:
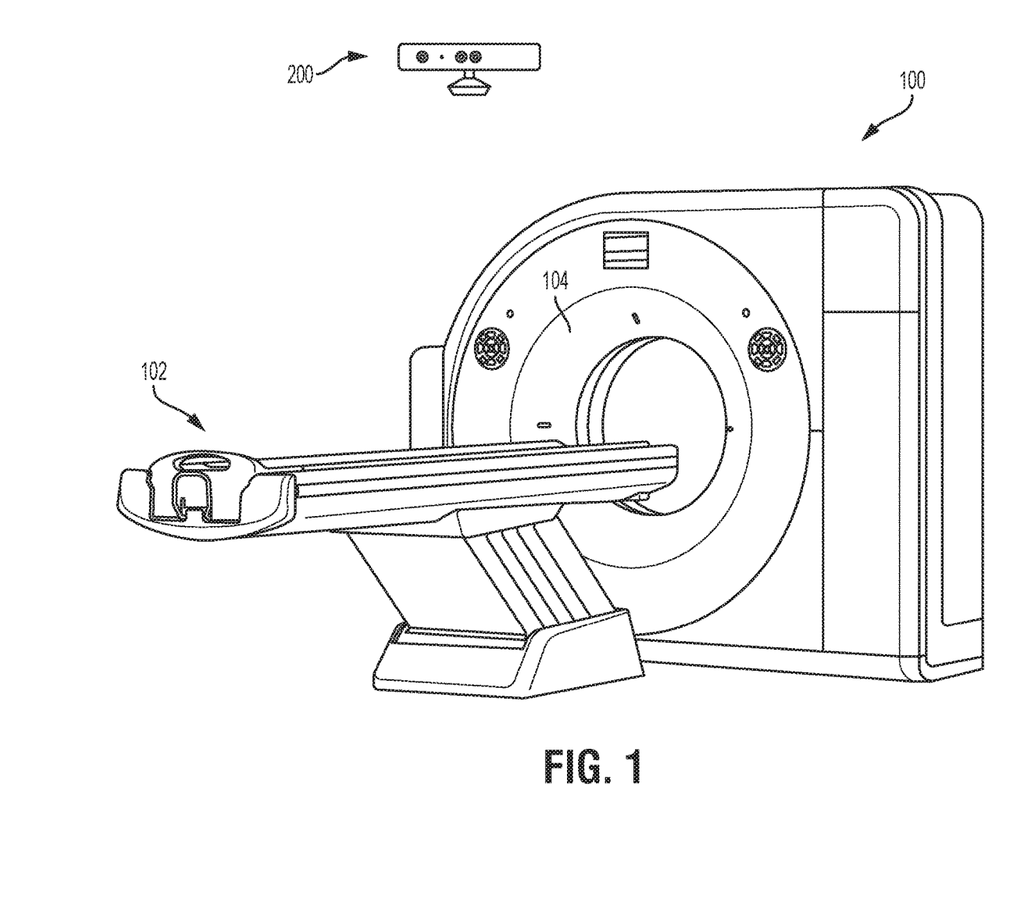
FIG. 1 illustrates a system for performing dose-optimized CT acquisition for a target organ of a patient according to an exemplary embodiment of the present invention.

FIG. 1 illustrates a system for performing dose-optimized CT acquisition for a target organ of a patient according to an exemplary embodiment of the present invention. As shown in FIG. 1 a CT scanner 100 includes a table 102 and a gantry 104. The gantry includes an x-ray source (e.g., x-ray tube) and x-ray detectors located directly opposite the x-ray source. The table 102 and the gantry 104 are motorized and movement of the table 102 and the gantry 104 controlled by a processor or controller in the CT scanner 100. During a spiral CT scan, the patient lies on the table 102, which slowly moves through the gantry 104 while the gantry 104 rotates around the patient on the table 102. As the gantry 104 rotates around the patient, the x-ray source shoots narrow beams of x-rays through the patient's body, and as the x-rays beams leave the patient's body, they are picked up by the x-ray detectors and transmitted to a computer. The computer constructs 2D image slices of the patient from the detected x-ray beams and the table 102 is moved incrementally in the gantry 104 until the spiral CT scan is complete. The 2D image slices can be used to reconstruct a 3D CT volume.

As shown in FIG. 1, in an advantageous embodiment, a 3D camera 200 can be positioned above the table 102 of the CT scanner 100. The 3D camera 200 is a camera that provides depth information along with typical image information, such as RGB (Red, Green, Blue) data. For example, the 3D camera 200 can be a structured light based camera (such as Microsoft Kinect or ASUS Xtion), a stereo camera, or a time of flight camera (such as Creative TOF camera). The image data obtained from the 3D camera 200 is typically referred to as an RGBD (RGB+Depth) image, which includes an RGB image, in which each pixel has an RGB value, and a depth image, in which the value of each pixel corresponds to a depth or distance of the pixel from the camera. In an advantageous implementation, the 3D camera 200 can be located at a fixed position with respect to the CT scanner 100 such that a transformation between a coordinate system of the 3D camera 200 and a coordinate system of the CT scanner 100 is known. For example, the 3D camera 200 can be mounted on a ceiling at a fixed point above the table 102 of the CT scanner 100. A computer can communicate with both the CT scanner 100 and the 3D camera 200 to control image acquisition by both the CT scanner 100 and the 3D camera 200.

In an advantageous embodiment of the present invention, scan planning for acquiring a CT scan of a target organ can be performed as follows. A patient lies on the table 102 of the CT scanner 100 and the 3D camera 200 acquires a 3D profile (e.g. RGBD image) of the patient on the table 102. A patient model can then be fit to the 3D profile of the patient in order to estimate the anatomical location of the target organ (e.g. lungs) in the 3D profile. A start confidence range is computed before the target organ (e.g., above (toward the patient's head) the target organ if the patient enters the gantry 104 head first). An end confidence range may also be computed after the target organ (e.g., below (toward the patient's feet) the target organ if the patient enters the gantry 104 head first). The table 102 is automatically moved to position the patient at or before the beginning of the estimated start confidence range before the target organ, and the CT scanner 100 begins acquisition of a localizer spiral CT scan. The localizer spiral CT scan is a "low-intensity" spiral CT acquisition (i.e., acquisition acquired while rotating the gantry 104 around the patient), that is performed with a first x-ray intensity that is lower than a second x-ray intensity used for a diagnostic scan of the target organ. The radiation x-ray intensity of the localizer spiral CT scan can be a predetermined x-ray intensity (e.g., set based on individual settings of the CT scanner 100) that is just high enough to acquire image information for an initial screening to determine an extent of the target organ, as a lower image quality is acceptable in the localizer CT scan than is required to make a diagnostic assessment of the target organ. The localizer CT spiral scan is considered to be a "low-intensity" scan because it utilizes a smaller x-ray intensity relative to the diagnostic scan, resulting in less radiation dose to which the patient is exposed. Real time spiral images from the localizer spiral CT scan are then automatically analyzed, possibly in combination with 3D patient model fit to the 3D profile, in order to automatically predict a starting location of the target organ, for example by detecting proximity of a landmark (e.g., the lung apex) indicating the beginning of the target organ. Once proximity to the starting location of the target organ is detected, the x-ray intensity is driven up to a higher level configured for diagnostic scanning of the target organ and the spiral CT scan continues, with the diagnostic spiral CT scan beginning at the predicted starting location of the target organ. This seamlessly begins the diagnostic spiral CT scan after the localizer spiral CT scan of the exploration region (confidence range) before the target organ. Real time images from the diagnostic CT scan are then automatically analyzed to detect or predict a location at which full coverage of the target organ is reached. For example, the prior information in the 3D profile for the patient can be used to predict the end location of the target organ. The spiral CT acquisition is controlled to automatically stop at the predicted end location of the target organ, or after it is detected that the target organ has been fully scanned. This method for scan planning and acquisition is described in greater detail in connection with FIG. 2 below.

Figure 2:
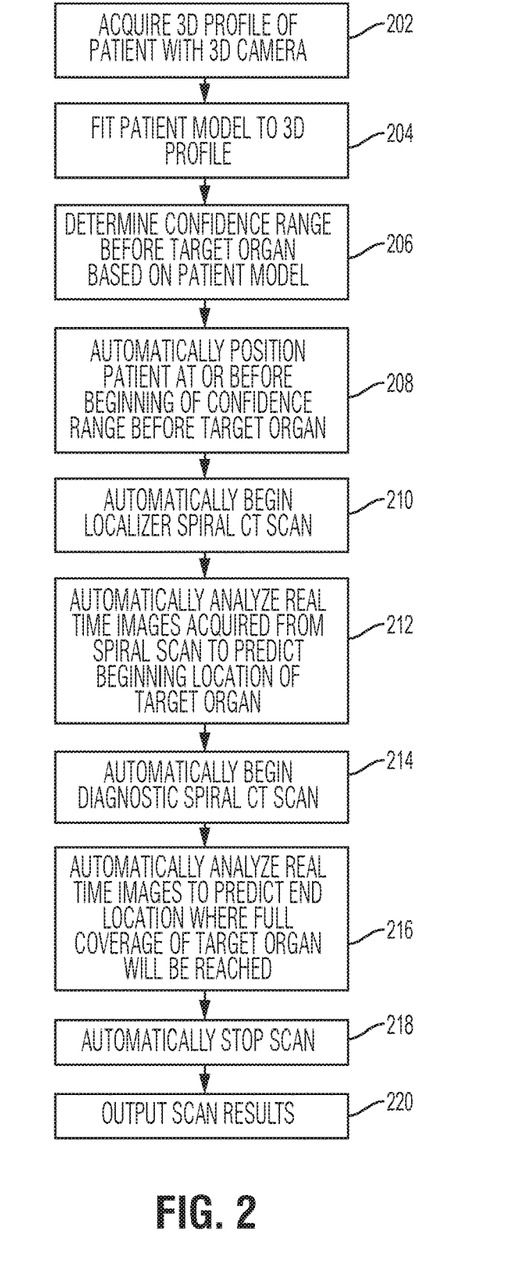
FIG. 2 illustrates a method for dose-optimized acquisition of a CT scan for a target organ according to an embodiment of the present invention.

FIG. 2 illustrates a method for dose-optimized acquisition of a CT scan for a target organ according to an embodiment of the present invention. Referring to FIG. 2, at step 202, a 3D profile of a patient on a table of a CT scanning device is acquired using a 3D camera. The 3D camera can be located at a predetermined position with respect to the CT scanning device, such as on a ceiling above the table of CT scanning device. In an advantageous implementation, the 3D camera is used to acquire an RGBD image of the patient's body is taken from above the patient while the patient is lying on the table. The table can be positioned at a predetermined position when the RGBD image of the patient is acquired. Since the position of the 3D camera with respect to the table is known, the RGBD image can then be converted into a 3D point cloud in a coordinate system of the table of the CT scanning device. The 3D camera can be controlled by a processor of a computer system to acquire the RGBD image of the patient, and the acquired RGBD image can then be received by the computer system, which can then generate the 3D profile of the patient by converting the RGBD image into a 3D point cloud in the coordinate system of the table.

At step 204 a patient model is fit to the 3D profile of the patient to estimate the anatomical location of the target organ of the patient. In an advantageous embodiment, the patient model is a statistical model of a patient body that includes the anatomical location of at least the target organ (e.g., the lungs). For example, the statistical model can include relative locations of multiple anatomical structures and organs including the target organ. The statistical model can then be registered to the 3D profile, e.g. with an iterative closest point algorithm. In a possible implementation, a rigid registration can be determined that minimizes a difference between the point cloud and the patient body model. In another possible implementation, a rigid registration and a non-rigid deformation can be combined for the same purpose. In yet another implementation, different patient models may be provided according to age, gender, body type, etc., and the model that most closely resembles the patient on the table is selected. The selected model is then registered to the 3D profile of the patient with rigid and possible non-rigid registration. Once the patient model is fit to the 3D profile of the patient, the patient model provides an estimated location of the target organ with respect to the table of the CT scanning device. In an exemplary embodiment, patient model can be fit to the 3D profile using the methods described in U.S. Pat. No. 9,524,582, entitled "Method and System for Constructing Personalized Avatars Using a Parametrized Deformable Mesh", and International Patent Publication No. WO 2016/073841 A1, entitled "Scan Data Retrieval with Depth Sensor Data", which are incorporated herein by reference in their entirety.

At step 206, a confidence range before the target organ is determined based on the patient model. The patient model provides an estimated anatomical location and boundary of the target organ. Using the estimated boundary of the target organ, a predetermined size confidence range or "landing zones" is determined before the estimated boundary of the target organ in the scanning direction. This confidence range or landing zone before the target organ in the scanning direction is referred to herein as the start confidence range or start landing zone. In a possible implementation, a predetermined size end confidence range or landing zone after the target organ in the scanning direction may also be determined. For example, if a patient is positioned to be scanned head first on the table, the start confidence range or "landing zone" can be determined to extend a predetermined distance above (toward the patient's head) the uppermost point on the estimated organ boundary and the end confidence range or "landing zone" can be determined to extend a predetermined distance below (toward the patient's feet) the lowermost point on the estimated organ boundary. If the patient is positioned to be scanned feet first, these landing zones are reversed. For a CT lung scan, the start confidence range can be determined as a region extending a predetermined distance above an estimated location of a lung apex in the patient model and the end confidence rang can be determined as a region extending a predetermined distance below an estimated location of a lung lobe tip in the patient model. The start confidence range is used to determine the starting location of the CT acquisition. The end confidence range may be used to provide an estimate of the ending location of the CT acquisition, which is ultimately refined by the real-time CT information acquired during the CT acquisition. In a possible implementation, the end confidence range may be omitted and the ending location of the CT acquisition determined only from the real-time CT information acquired during the CT acquisition.

At step 208, the patient is automatically positioned at or before the beginning of the start confidence range before the target organ. In particular, once the location of the confidence range before the target organ in the coordinate system of the table is determined (in step 206), the table is controlled to position the patient such that the scanning can be started at the beginning of the start confidence range before the target organ. When the table will be moved in the scanning direction during the scanning, the scanning will start with the start confidence range before the target organ then continue with the target organ. It is to be understood that the table movement may be started with the patient before the beginning of the start confidence range, and the X-ray source will be activated to begin scanning at the beginning of the start confidence range. Since the patient model provides an approximate organ boundary for the target organ, the start confidence range before the target organ ensures that the scan does not miss the beginning of the target organ.

At step 210, a localizer spiral scan is automatically started at the beginning of the confidence range before the target organ. The localizer spiral CT scan is a spiral CT acquisition (i.e., acquisition acquired while rotating the gantry around the patient), that is performed with a first x-ray intensity that is lower than a second x-ray intensity used for a diagnostic scan of the target organ. The x-ray intensity of the localizer spiral CT scan can be a predetermined x-ray intensity (e.g., set based on individual settings of the CT scanner) that is high enough to acquire image information for an initial screening to determine an extent of the target organ, but lower than the x-ray intensity used for a diagnostic scan of the target organ, as a lower image quality is acceptable in the localizer spiral CT scan than is required to make a diagnostic assessment of the target organ. The localizer spiral CT scan is considered to be a "low-intensity" scan because it utilizes a smaller x-ray intensity relative to the diagnostic scan, in order to reduce the radiation dose to the patient. The table is controlled to move through the gantry in the scanning direction while the low-intensity spiral scan is being performed.

At step 212, real time localizer scan images acquired from the localizer spiral CT scan are automatically analyzed to predict a beginning location of the target organ. In an advantageous embodiment, images acquired from the localizer spiral CT scan are processed or "scanned" by the computer system in real time or near real time as they are acquired to detect proximity to an anatomic landmark that indicates the beginning of the target organ. For a CT lung scan, proximity to the lung apex can be automatically detected in the real time images acquired from the localizer spiral scan. In a first embodiment, the real time localizer scan images that are used to predict the beginning location of the target organ are 2D projection images acquired by the CT scanner during the localizer spiral CT scan. In a second embodiment, the real time localizer scan images that are used to predict the beginning location of the target organ are reconstructed 2D cross-sectional CT image slices that are reconstructed from the projection images acquired during the localizer spiral CT scan. In a third embodiment, the real time localizer scan images that are used to predict the beginning location of the target organ are reconstructed 3D images that are reconstructed from the projection images acquired during the localizer spiral CT scan. As used herein, analyzing real time localizer scan images means that the localizer scan images (e.g., 2D projection images, reconstructed cross-sectional CT image slices, or reconstructed 3D images) are processed as they are acquired during the scan, instead of after the scan is completed. In the second and third embodiments, in which the cross-sectional CT image slices and reconstructed 3D images are used, respectively, real time means that the reconstruction is performed "on-the-fly" during the scan, not after the scan is completed.

In an advantageous embodiment, machine learning based landmark detection may be used to detect an anatomic landmark or several landmarks that are used to estimate a predicted beginning location of the target organ in the real-time localizer scan images. The landmarks can provide an indicator that the beginning of the target organ is close before it actually appears in the scan, which makes it possible to start the high-intensity diagnostic scan based on the anticipated start of the target organ. In an advantageous embodiment, the machine learning algorithm is not simply trained on individual landmarks but includes the relation between these landmarks. For example, the machine learning algorithm can learn a relationship between anatomical landmarks detectable in the start confidence range before the target organ (e.g. vertebrae in the spine, anatomical landmarks from nearby organs, etc.) and at least one anatomical landmark that corresponds to a beginning of the target organ (e.g., lung apex). In an offline training phase, one or more landmark detectors can be trained from annotated training images to detect anatomical landmarks in the start confidence range (e.g., vertebrae, anatomical landmarks from nearby organs, etc.) and to estimate a predicted location of the anatomical landmark corresponding to the beginning of the target organ (e.g., lung apex) based on the detected anatomical landmarks in the start confidence range. The one or more trained landmark detectors can then be used to automatically detect the anatomical landmarks in the start confidence range (e.g., vertebrae, landmarks from nearby organs, etc.) in the real-time localizer spiral scan images, estimate a predicted location of a landmark corresponding to the beginning of the target organ based on the detected landmarks in the start confidence range, and use the predicted beginning location to determine when the scan is near (e.g., a predetermined distance from) the predicted beginning location of the target organ. In an exemplary implementation, the trained landmark detectors for detecting anatomical landmarks in the start confidence range can be machine-learning based discriminative classifiers, such as a probabilistic boosting tree (PBT) detector, and the trained landmark detector for estimating a predicted beginning location of the target organ based on the other detected landmarks can be a trained machine-learning based regressor. However, it is to be understood that other machine learning algorithms can be used for training the landmark detectors as well. In an exemplary embodiment, anatomical landmarks and organs can be detected in the localizer CT images using methods described in United States Patent Application Publication No. 2010/0080434, entitled "Method and System for Hierarchical Parsing and Semantic Navigation of Full Body Computed Tomography Data", which is incorporated herein by reference in its entirety. The training images used to train the trained landmark detectors can be previously stored localizer scan images (e.g., either projection images or cross-sectional CT images) acquired from previous localizer spiral CT scans.

At step 214, a diagnostic spiral CT scan is automatically started at the predicted beginning location of the target organ. The localizer spiral CT scan continues at the first x-ray intensity until the beginning of the target organ is anticipated in the real-time localizer scan images and proximity to the predicted start location of is detected (e.g., it is determined that the scan is within a predetermined distance of the predicted start location of the target organ). Once proximity to predicted location of the anatomical landmark (e.g., lung apex) indicating the beginning of the target landmark is detected, the x-ray intensity is automatically adjusted to drive the x-ray intensity up to the second x-ray intensity used for a diagnostic scan of the target organ, such that the diagnostic part of the CT scan of the target organ starts at the predicted beginning location of the target organ. Since there will be a slight time delay between acquiring the localizer scan images, detecting the landmarks and estimating the beginning location of the target organ, and providing this information back to the CT scanner to control the CT scanner to increase the x-ray intensity, anticipating/predicting the beginning location of the target organ allows the CT scanner to be controlled to increase the x-ray intensity and start the diagnostic scan at the beginning location of the target organ. The second x-ray intensity used for the diagnostic spiral CT scan is greater than the first x-ray intensity used for the localizer spiral CT scan. The second x-ray intensity can be a predetermined x-ray intensity that for a diagnostic scan of the target organ that corresponds to a preset protocol for scanning the target organ and/or a preset scanning protocol of the particular CT scanner. This x-ray intensity may vary depending on which organ is being scanned and/or what CT scanner is used. Since a CT spiral scan was already being performed (at the lower x-ray intensity), the diagnostic spiral CT scan is started seamlessly at the predicted beginning location of the target organ estimated from the localizer scan images in the exploration region (start confidence range) without having to stop and re-start the gantry.

At step 216, real time diagnostic scan images from the diagnostic spiral CT scan are automatically analyzed to estimate where full coverage of the target organ is reached. In an advantageous embodiment, images acquired from the diagnostic spiral CT scan are processed by the computer system in real time or near real time as they are acquired estimate/predict an end location of the target organ at which full coverage of the target organ will be reached. In a first embodiment, the real time diagnostic scan images that are used to predict the end location of the target organ are 2D projection images acquired by the CT scanner during the diagnostic spiral CT scan. In a second embodiment, the real time diagnostic scan images that are used to predict the end location of the target organ are reconstructed cross-sectional CT image slices that are reconstructed from the projection images acquired during the diagnostic spiral CT scan. In a third embodiment, the real time localizer scan images that are used to predict the end location of the target organ are reconstructed 3D images that are reconstructed from the projection images acquired during the diagnostic spiral CT scan. As used herein, analyzing real time diagnostic scan images means that the diagnostic scan images (e.g., 2D projection images, reconstructed cross-sectional CT image slices, or reconstructed 3D images) are processed as they are acquired during the scan, instead of after the scan is completed. In the second and third embodiments, in which the cross-sectional CT image slices and reconstructed 3D images are used, respectively, real time means that the reconstruction is performed "on-the-fly" during the scan, not after the scan is completed.

In an advantageous embodiment, learning based landmark detection and/or organ model estimation may be used to detect one or more anatomic landmarks and/or estimate an organ model in the real-time diagnostic scan images. The estimated landmarks (e.g., lung landmarks, diaphragm, etc.) detected in the real time diagnostic scan images and/or an organ model of the target organ estimated in the real time diagnostic scan images can provide an indicator that the end of the target organ is close before it actually appears in the scan, which makes it possible to anticipated the end location of the target organ in order to end the diagnostic spiral CT scan upon reaching the predicted end location of the target organ. For example, in an offline training phase, landmark detectors can be trained from annotated training images to detect anatomic landmarks (e.g., lung landmarks, diaphragm, etc.) in the diagnostic scan images and machine learning based classifiers can be used to estimate a pose of an organ model in the diagnostic images based on the detected landmarks. Then trained landmark detectors can then be used to automatically detect the landmarks in the real-time diagnostic spiral scan images and the trained machine leaning based classifiers can be used to estimate the organ model to the real time diagnostic scan images. The estimated organ model can then be used to predict a location of a landmark indicating of the end location of the target organ (e.g., lung lobe tip) in the diagnostic scan images. The trained detectors/classifiers can be trained using any machine learning algorithm, such as a probabilistic boosting tree (PBT). The training images can be previously stored spiral scan images (e.g., projection images or cross-sectional CT images) acquired from diagnostic spiral CT scans. In an exemplary embodiment, anatomical landmarks can be detected and organ models can be segmented in the diagnostic CT images using methods described in United States Patent Application Publication No. 2010/0080434, entitled "Method and System for Hierarchical Parsing and Semantic Navigation of Full Body Computed Tomography Data", which is incorporated herein by reference in its entirety. In a possible embodiment, information from the real-time diagnostic spiral scan images can be combined with the previously computed patient model to update the anatomical organ models. The patient model computed from the 3D patient profile estimates organ locations based on the exterior body shape. The diagnostic spiral CT scan provides interior information, and the organ models may be updated based in the CT image information. The updated organ models can be used to predict the location at which the target organ ends before full coverage of the target organ is achieved by the scan. It is to be understood that although the previous patient model computed from the 3D profile may be updated to generate an organ model that is used to predict the end location, the present invention is not limited thereto, and a separate organ model may be estimated from the CT image information in the diagnostic scan images.

At step 218, the CT scan of the target organ is automatically stopped once the predicted end location of the target organ is reached. For example, in response to determination that a proximity to the predicted end location has been reached (e.g., the scan is within a predetermined distance from the end location), the CT scanner can be controlled to stop the diagnostic spiral CT scan immediately after the predicted end position of the target organ has been scanned. Since there will be a slight time delay between acquiring the diagnostic scan images, detecting landmarks and/or an organ model and estimating the end location of the target organ, and providing this information back to the CT scanner to control the CT scanner to stop the scan, anticipating/predicting the end location of the target organ allows the CT scanner to be controlled to stop the diagnostic CT spiral scan immediately after the predicted end position of target organ has been scanned, thus ensuring that full coverage of the target organ has been reached and preventing the patient from being exposed to radiation beyond what is necessary to achieve full coverage of the target organ.

At step 220, results of the CT scan of the target organ are output. In particular, a 3D CT volume including the target organ is reconstructed from the projection images acquired during the diagnostic CT scan of the target organ. The 3D CT volume can be displayed on a display device. The 3D CT volume can be displayed using a 3D visualization and/or visualizations of various 2D slices of the 3D CT volume. The 3D CT volume can be displayed in an interactive user interface that allows a user to interact with the displayed 3D CT volume.

In a possible embodiment, once the diagnostic CT scan of the target organ is finalized, the target organ (e.g., lungs) can be automatically segmented in the 3D CT volume, resulting in the determination of the anatomical pose of the target organ in the 3D CT volume. For example, marginal space learning (MSL), in which the anatomical pose information is estimated in a series of marginal search spaces of increasing dimensionality using respective trained machine learning based classifiers for each marginal search space, can be used to segment the target organ and determine the anatomical pose of the target organ in the 3D CT volume. Reconstruction boxes can then be automatically aligned to the target organ based on the detected anatomical pose of the target organ. The computed reconstruction boxes can then be used to perform reconstructions of the projection images acquired in the diagnostic scan in order to generate a reconstructed 3D volume whose axes are aligned with the target organ. This aligned reconstructed 3D volume can be displayed on a display device.

The above describe method for dose-optimized acquisition of a CT scan for a target organ can be used to automatically perform a CT lung examination from patient positioning to image reconstruction without manual intervention and without time penalties due to acceleration/stopping times for the gantry rotation. Additionally, overall dose (topographic+tomographic scans) can be reduced, as compared to conventional methods.

The method of FIG. 2 utilizes a 3D camera to generate a 3D profile, which is used to automatically position the patient prior to the localizer spiral CT scan. In an alternative embodiment of the present invention, the method may be performed without a 3D camera. In this case, user input can substitute for the information from the 3D camera. In particular, a user input that prescribes an approximate start of the scan range can be received. The method then continues from step 208 in FIG. 2. The patient is positioned at or before the beginning of the prescribed start of the scan range (confidence range) and the localizer spiral CT scan is started at the prescribed start of the scan range. The real-time localizer scan images are automatically analyzed to estimate/predict the beginning location of the target organ, and the diagnostic spiral CT scan is automatically started in response to detection of proximity to the predicted beginning location of the target organ in the real-time localizer scan images. The real-time diagnostic scan images are anatomically analyzed to estimate/predict an end location of the target organ where full coverage of the target organ will be reached, and the scan is automatically stopped once the predicted end position of the target organ has been scanned.

Figure 3:
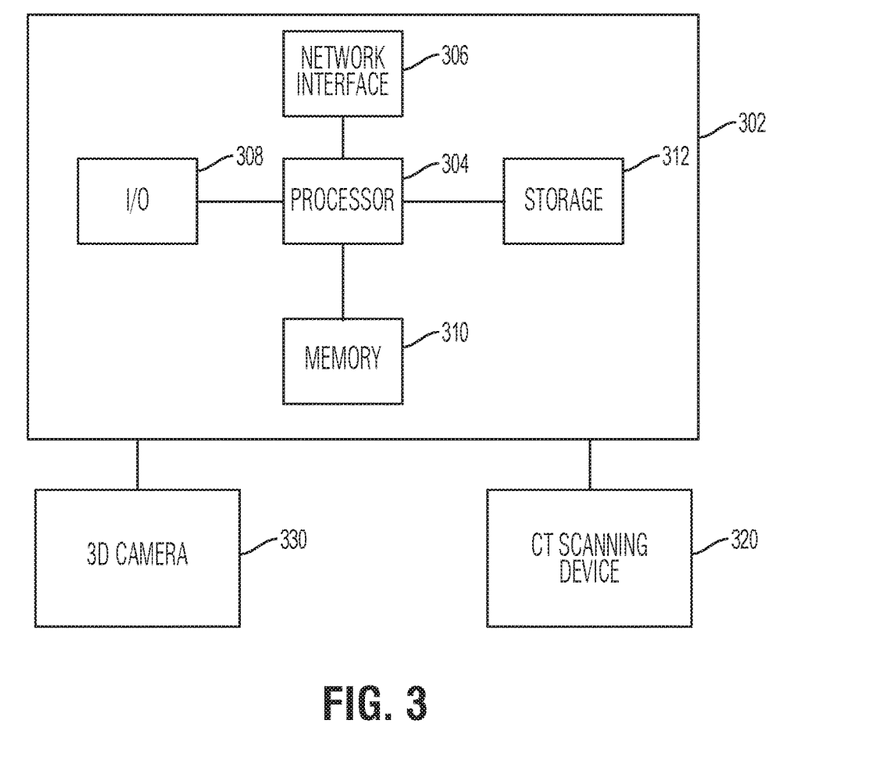
FIG. 3 is a high-level block diagram of a computer capable of implementing the present invention.

In another alternative embodiment of the present invention, the method for dose-optimized acquisition of a CT scan of a target organ may be implemented using a 2D camera, such as a standard 2D digital camera, instead of the 3D camera to determine the start confidence range before the target organ. In this case, an anatomical model may be estimated for the patient based on a 2D image (e.g., digital photograph) acquired using the 2D camera, for example by registering a statistical model of a patient body to the 2D image using a 2D/3D registration technique for a 3D anatomical model or a 2D/2D registration technique for a 2D anatomical model. The method then continues at step 206 and determines the confidence range before the target organ based on the patient model that was registered based on the 2D image The above-described methods for dose-optimized acquisition of a CT scan of a target organ may be implemented on a computer using well-known computer processors, memory units, storage devices, computer software, and other components. A high-level block diagram of such a computer is illustrated in FIG. 3. Computer 302 contains a processor 304, which controls the overall operation of the computer 302 by executing computer program instructions which define such operation. The computer program instructions may be stored in a storage device 312 (e.g., magnetic disk) and loaded into memory 310 when execution of the computer program instructions is desired. Thus, the steps of the methods of FIG. 2 may be defined by the computer program instructions stored in the memory 310 and/or storage 312 and controlled by the processor 304 executing the computer program instructions. A CT scanning device 320 can be connected to the computer 302 to input image data to the computer 302. It is possible to implement the CT scanning device 320 and the computer 302 as one device. It is also possible that the CT scanning device 320 and the computer 302 communicate wirelessly through a network or wireless communication protocol. The processor 304 of the computer 302 can control operations of the CT scanning device 320. In a possible embodiment, the computer 302 may be located remotely with respect to the CT scanning device 320 and the method steps are performed as part of a server or cloud based service. A 3D camera 330 can be connected to the computer 302 to input image data to the computer 302. The 3D camera 330 can be connected to the computer 302 via a wire or the 3D camera 330 and the computer 302 may communicate wirelessly via a network or wireless communication protocol. The processor 304 of the computer 302 can control operations of the 3D camera 330. The computer 302 also includes one or more network interfaces 306 for communicating with other devices via a network. The computer 302 also includes other input/output devices 308 that enable user interaction with the computer 302 (e.g., display, keyboard, mouse, speakers, buttons, etc.). One skilled in the art will recognize that an implementation of an actual computer could contain other components as well, and that FIG. 3 is a high level representation of some of the components of such a computer for illustrative purposes.

The above-described methods for dose-optimized acquisition of a CT scan of a target organ may be implemented using computers operating in a client-server relationship. Typically, in such a system, the client computers are located remotely from the server computer and interact via a network. The client-server relationship may be defined and controlled by computer programs running on the respective client and server computers.

The above-described methods for medical image synthesis may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIG. 2. Certain steps of the methods described herein, including one or more of the steps of FIG. 2, may be performed by a server or by another processor in a network-based cloud-computing system. Certain steps of the methods described herein, including one or more of the steps of FIG. 2, may be performed by a client computer in a network-based cloud computing system. The steps of the methods described herein, including one or more of the steps of FIG. 2, may be performed by a server and/or by a client computer in a network-based cloud computing system, in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for dose-optimized acquisition of a computed tomography (CT) scan of a target organ, comprising:
   starting a localizer spiral CT scan at a beginning of a confidence range before a target organ of a patient;
   receiving real-time localizer scan images from the localizer spiral CT scan as a patient is moved relative to a gantry of a CT scanning device;
   automatically analyzing the real-time localizer scan images to predict a beginning location of the target organ based on the real-time localizer scan images;
   automatically starting a diagnostic spiral CT scan at the predicted beginning location of the target organ;
   receiving real-time diagnostic scan images from the diagnostic spiral CT scan as the patient is moved relative to the gantry of the CT scanning device;
   automatically analyzing the real-time diagnostic scan images to predict an end location of the target organ where full coverage of the target organ will be reached based on the real-time diagnostic scan images; and
   automatically stopping the diagnostic spiral CT scan in response to reaching the predicted end location of the target organ.

2. The method of claim 1, wherein automatically analyzing the real-time localizer scan images to predict a beginning location of the target organ based on the real-time localizer scan images comprises:
   detecting one or more anatomical landmarks in the confidence range before the target organ in the real-time localizer scan images using one or more trained landmark detectors;
   automatically estimating the beginning location of the target organ based on the one or more landmarks in the confidence range before the target organ detected in the in the real-time localizer scan images.

3. The method of claim 1, wherein automatically analyzing the real-time diagnostic scan images to predict an end location of the target organ where full coverage of the target organ will be reached based on the real-time diagnostic scan images comprises:
automatically estimating an organ model of the target organ in the real-time diagnostic scan images; and
automatically estimating the end location of the target organ from the estimated organ model of the target organ.

4. The method of claim 3, wherein estimating an organ model of the target organ in the real-time diagnostic scan images comprises:
detecting one or more anatomical landmarks in the real-time diagnostic scan images using one or more trained landmark detectors; and
fitting the organ model of the target organ to the real-time diagnostic scan images based on the one or more anatomical landmarks detected in the real-time diagnostic scan images.

5. The method of claim 1, further comprising:
acquiring a 3D profile of the patient on a table of the CT scanning device using a 3D camera;
fitting a patient model to the 3D profile of the patient; and
automatically determining the beginning of the confidence range before the target organ of the patient based on the patient model.

6. The method of claim 5, wherein acquiring a 3D profile of the patient on a table of the CT scanning device using a 3D camera comprises:
receiving an RGBD image of the patient on the table of the CT scanning device from the 3D camera; and
converting the RGBD image into a 3D point cloud in a coordinate system of the table of the CT scanning device.

7. The method of claim 6, wherein fitting a patient model to the 3D profile of the patient comprises:
registering a statistical shape model of a patient body including an anatomical location of the target organ to the 3D point cloud in the coordinate system of the table of the CT scanning device.

8. The method of claim 1, wherein the real-time localizer scan images are one of 2D projection images, reconstructed cross-sectional CT image slices, or reconstructed 3D images.

9. The method of claim 1, wherein the real-time diagnostic scan images are one of 2D projection images, reconstructed cross-sectional CT image slices, or reconstructed 3D images.

10. The method of claim 1, wherein the localizer spiral CT scan uses an x-ray intensity and the diagnostic spiral CT scan uses an x-ray intensity that is greater than the first x-ray intensity.

11. The method of claim 1, further comprising:
reconstructing a 3D CT volume including the target organ from the diagnostic spiral CT scan.

12. The method of claim 1, further comprising:
detecting an anatomical pose of the target organ in a 3D CT volume resulting from the diagnostic spiral CT scan;
automatically aligning reconstruction boxes to target organ based on the detected anatomical pose of the target organ; and
generating a reconstructed 3D CT volume with axes aligned to the anatomical pose of the target organ using the aligned reconstruction boxes.

13. The method of claim 1, wherein the target organ is the lungs.

14. The method of claim 13, wherein automatically analyzing the real-time localizer scan images to predict a beginning location of the target organ based on the real-time localizer scan images comprises:
automatically predicting a lung apex location based on the real-time localizer scan images prior to the lung apex location appearing in the real-time localizer scan images.

15. The method of claim 11, wherein automatically analyzing the real-time diagnostic scan images to predict an end location of the target organ where full coverage of the target organ will be reached based on the real-time diagnostic scan images comprises:
automatically predicting a lung lobe tip location based on the real-time diagnostic scan images prior to the lung lobe tip location appearing in the real-time localizer scan images.

16. The method of claim 1, further comprising:
acquiring a 2D image of the patient on a table of the CT scanning device using a 2D camera;
registering a patient model to the 2D image of the patient; and
automatically determining the beginning of the confidence range before the target organ of the patient based on the patient model.

17. An apparatus for dose-optimized acquisition of a computed tomography (CT) scan of a target organ, comprising:
means for starting a localizer spiral CT scan at a beginning of a confidence range before a target organ of a patient;
means for receiving real-time localizer scan images from the localizer spiral CT scan as a patient is moved relative to a gantry of a CT scanning device;
means for automatically analyzing the real-time localizer scan images to predict a beginning location of the target organ based on the real-time localizer scan images;
means for automatically starting a diagnostic spiral CT scan at the predicted beginning location of the target organ;
means for receiving real-time diagnostic scan images from the diagnostic spiral CT scan as the patient is moved relative to the gantry of the CT scanning device;
means for automatically analyzing the real-time diagnostic scan images to predict an end location of the target organ where full coverage of the target organ will be reached based on the real-time diagnostic scan images; and
means for automatically stopping the diagnostic spiral CT scan in response to reaching the predicted end location of the target organ.

18. The apparatus of claim 17, wherein the means for automatically analyzing the real-time localizer scan images to predict a beginning location of the target organ based on the real-time localizer scan images comprises:
means for detecting one or more anatomical landmarks in the confidence range before the target organ in the real-time localizer scan images using one or more trained landmark detectors;
means for automatically estimating the beginning location of the target organ based on the one or more landmark landmarks in the confidence range before the target organ detected in the in the real-time localizer scan images.

19. The apparatus of claim 17, wherein the means for automatically analyzing the real-time diagnostic scan images to predict an end location of the target organ where full coverage of the target organ will be reached based on the real-time diagnostic scan images comprises:
 means for automatically estimating an organ model of the target organ in the real-time diagnostic scan images; and
 means for automatically estimating the end location of the target organ from the estimated organ model of the target organ.

20. The apparatus of claim 17, further comprising:
 means for acquiring a 3D profile of the patient on a table of the CT scanning device using a 3D camera;
 means for fitting a patient model to the 3D profile of the patient; and
 means for automatically determining the beginning of the confidence range before the target organ of the patient based on the patient model.

21. The apparatus of claim 17, wherein the real-time localizer scan images are one of 2D projection images, reconstructed cross-sectional CT image slices, or reconstructed 3D images received in real-time from the localizer spiral CT scan, and the real-time diagnostic scan images are one of 2D projection images, reconstructed cross-sectional CT image slices, or reconstructed 3D images received in real-time from the diagnostic spiral CT scan.

22. The apparatus of claim 17, wherein the localizer spiral CT scan uses a first x-ray intensity and the diagnostic spiral CT scan uses a second x-ray intensity that is greater than the first x-ray intensity.

23. The apparatus of claim 17, wherein the target organ is the lungs, the means for automatically analyzing the real-time localizer scan images to predict a beginning location of the target organ based on the real-time localizer scan images comprises means for automatically predicting a lung apex location based on the real-time localizer scan images prior to the lung apex location appearing in the real-time localizer scan images, and the means for automatically analyzing the real-time diagnostic scan images to predict an end location of the target organ where full coverage of the target organ will be reached based on the real-time diagnostic scan images comprises means for automatically predicting a lung lobe tip location based on the real-time diagnostic scan images prior to the lung lobe tip location appearing in the real-time localizer scan images.

24. A non-transitory computer readable medium storing computer program instructions for dose-optimized acquisition of a computed tomography (CT) scan of a target organ, the computer program instructions when executed by a processor cause the processor to perform operations comprising:
 starting a localizer spiral CT scan at a beginning of a confidence range before a target organ of a patient;
 receiving real-time localizer scan images from the localizer spiral CT scan as a patient is moved relative to a gantry of a CT scanning device;
 automatically analyzing the real-time localizer scan images to predict a beginning location of the target organ based on the real-time localizer scan images;
 automatically starting a diagnostic spiral CT scan at the predicted beginning location of the target organ;
 receiving real-time diagnostic scan images from the diagnostic spiral CT scan as the patient is moved relative to the gantry of the CT scanning device;
 automatically analyzing the real-time diagnostic scan images to predict an end location of the target organ where full coverage of the target organ will be reached based on the real-time diagnostic scan images; and
 automatically stopping the diagnostic spiral CT scan in response to reaching the predicted end location of the target organ.

25. The non-transitory computer readable medium of claim 24, wherein automatically analyzing the real-time localizer scan images to predict a beginning location of the target organ based on the real-time localizer scan images comprises:
 detecting one or more anatomical landmarks in the confidence range before the target organ in the real-time localizer scan images using one or more trained landmark detectors;
 automatically estimating the beginning location of the target organ based on the one or more landmark landmarks in the confidence range before the target organ detected in the in the real-time localizer scan images.

26. The non-transitory computer readable medium of claim 24, wherein automatically analyzing the real-time diagnostic scan images to predict an end location of the target organ where full coverage of the target organ will be reached based on the real-time diagnostic scan images comprises:
 automatically estimating an organ model of the target organ in the real-time diagnostic scan images; and
 automatically estimating the end location of the target organ from the estimated organ model of the target organ.

27. The non-transitory computer readable medium of claim 24, wherein the operations further comprise:
 acquiring a 3D profile of the patient on a table of the CT scanning device using a 3D camera;
 fitting a patient model to the 3D profile of the patient; and
 automatically determining the beginning of the confidence range before the target organ of the patient based on the patient model.

28. The non-transitory computer readable medium of claim 24, wherein the real-time localizer scan images are one of 2D projection images, reconstructed cross-sectional CT image slices, or reconstructed 3D images received in real-time from the localizer spiral CT scan, and the real-time diagnostic scan images are one of 2D projection images, reconstructed cross-sectional CT image slices, or reconstructed 3D images received in real-time from the diagnostic spiral CT scan.

29. The non-transitory computer readable medium of claim 24, wherein the localizer spiral CT scan uses a first x-ray intensity and the diagnostic spiral CT scan uses a second x-ray intensity that is greater than the first x-ray intensity.

30. The non-transitory computer readable medium of claim 24, wherein the target organ is the lungs, wherein automatically analyzing the real-time localizer scan images to predict a beginning location of the target organ based on the real-time localizer scan images comprises automatically predicting a lung apex location based on the real-time localizer scan images prior to the lung apex location appearing in the real-time localizer scan images, and wherein automatically analyzing the real-time diagnostic scan images to predict an end location of the target organ where full coverage of the target organ will be reached based on the real-time diagnostic scan images comprises automatically predicting a lung lobe tip location based on the real-time diagnostic scan images prior to the lung lobe tip location appearing in the real-time localizer scan images.

* * * * *